(12) United States Patent
Arbefeuille

(10) Patent No.: US 12,427,010 B2
(45) Date of Patent: *Sep. 30, 2025

(54) VASCULAR PROSTHESIS WITH CRIMPED ADAPTER AND METHODS OF USE

(71) Applicant: Bolton Medical, Inc., Sunrise, FL (US)

(72) Inventor: Samuel Arbefeuille, Sunrise, FL (US)

(73) Assignee: Bolton Medical, Inc., Sunrise, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 18/240,628

(22) Filed: Aug. 31, 2023

(65) Prior Publication Data

US 2024/0058114 A1    Feb. 22, 2024

Related U.S. Application Data

(60) Continuation of application No. 17/848,921, filed on Jun. 24, 2022, now Pat. No. 11,779,454, which is a
(Continued)

(51) Int. Cl.
*A61F 2/07* (2013.01)
*A61F 2/95* (2013.01)
(Continued)

(52) U.S. Cl.
CPC .................. *A61F 2/07* (2013.01); *A61F 2/95* (2013.01); *A61M 25/09* (2013.01);
(Continued)

(58) Field of Classification Search
CPC .... A61F 2/07; A61F 2/95; A61F 2/954; A61F 2/958; A61F 2/94; A61F 2/82;
(Continued)

(56) References Cited

U.S. PATENT DOCUMENTS 4,787,391 A    11/1988    Elefteriades
5,123,917 A     6/1992    Lee
(Continued)

FOREIGN PATENT DOCUMENTS

CN    104066401 A    9/2014
CN    203815663 U    9/2014
(Continued)

OTHER PUBLICATIONS

International Search Report and Written Opinion for International Application No. PCT/US2018/019350 dated May 15, 2018.
(Continued)

*Primary Examiner* — Seema Mathew
(74) *Attorney, Agent, or Firm* — Stephen J. Kenny; Emily H. Yasharpour; Foley Hoag LLP

(57) ABSTRACT

The vascular prosthesis includes a luminal graft component that defines at least one fenestration and a crimped adapter at the at least one fenestration. The crimped adapter includes a perimeter and an opening with a diameter smaller than the diameter of the fenestration, and includes a crimped portion of generally concentric folds about the opening. The opening can move relative to the perimeter region of the crimped adapter to accommodate positioning of a branch prosthesis extending through the crimped adaptor. The vascular prosthesis is implanted in a patient to thereby treat, for example, an arterial aneurysm that spans a region of an artery that includes at least one arterial branch.

18 Claims, 12 Drawing Sheets

Related U.S. Application Data division of application No. 16/414,208, filed on May 16, 2019, now Pat. No. 11,399,929, which is a continuation of application No. PCT/US2018/019350, filed on Feb. 23, 2018.

(60) Provisional application No. 62/463,063, filed on Feb. 24, 2017.

(51) Int. Cl.
  *A61M 25/09* (2006.01)
  *A61F 2/06* (2013.01)
  *A61F 2/82* (2013.01)
  *A61F 2/90* (2013.01)

(52) U.S. Cl.
  CPC ... *A61F 2002/061* (2013.01); *A61F 2002/075* (2013.01); *A61F 2002/821* (2013.01); *A61F 2/90* (2013.01); *A61F 2/9517* (2020.05)

(58) Field of Classification Search
  CPC .... A61F 2/915; A61F 2/856; A61F 2002/821; A61F 2/90; A61F 2002/065; A61F 2002/828; A61F 2/88; A61F 2250/006; A61F 2002/067; A61F 2/86; A61F 2230/0067; A61F 2/06; A61F 2002/823; A61F 2002/072; A61F 2220/0025; A61F 2230/006

See application file for complete search history.

(56) References Cited

U.S. PATENT DOCUMENTS

| | | | |
|---|---|---|---|
| 5,242,452 A | 9/1993 | Inoue | |
| 5,507,769 A | 4/1996 | Marin et al. | |
| 5,713,948 A | 2/1998 | Uflacker | |
| 5,755,769 A | 5/1998 | Richard et al. | |
| 5,873,906 A | 2/1999 | Lau et al. | |
| 5,984,955 A * | 11/1999 | Wisselink | A61F 2/954 |
| | | | 623/1.35 |
| 6,113,623 A | 9/2000 | Sgro | |
| 6,171,334 B1 | 1/2001 | Cox | |
| 6,280,464 B1 | 8/2001 | Hayashi | |
| 6,352,561 B1 | 3/2002 | Leopold et al. | |
| 6,395,018 B1 | 5/2002 | Castaneda | |
| 6,610,087 B1 | 8/2003 | Zarbatany et al. | |
| 6,645,242 B1 | 11/2003 | Quinn | |
| 6,776,791 B1 | 8/2004 | Stallings et al. | |
| 7,112,216 B2 | 9/2006 | Gregorich | |
| 7,189,257 B2 | 3/2007 | Schmitt et al. | |
| 7,326,242 B2 * | 2/2008 | Eidenschink | A61F 2/86 |
| | | | 623/1.35 |
| 7,435,253 B1 | 10/2008 | Hartley et al. | |
| 7,637,940 B2 | 12/2009 | Kocur et al. | |
| 7,645,298 B2 | 1/2010 | Hartley et al. | |
| 7,678,141 B2 * | 3/2010 | Greenan | A61F 2/07 |
| | | | 623/1.13 |
| 7,763,063 B2 | 7/2010 | Arbefeuille et al. | |
| 7,842,081 B2 | 11/2010 | Yadin | |
| 8,007,605 B2 | 8/2011 | Arbefeuille et al. | |
| 8,062,345 B2 | 11/2011 | Ouellette et al. | |
| 8,062,346 B2 | 11/2011 | Quigley et al. | |
| 8,062,349 B2 | 11/2011 | Moore et al. | |
| 8,070,790 B2 | 12/2011 | Berra et al. | |
| 8,128,686 B2 | 3/2012 | Paul, Jr. et al. | |
| 8,172,895 B2 | 5/2012 | Anderson et al. | |
| 8,236,040 B2 | 8/2012 | Mayberry et al. | |
| 8,277,501 B2 | 10/2012 | Chalekian et al. | |
| 8,292,943 B2 | 10/2012 | Berra et al. | |
| 8,298,278 B2 | 10/2012 | Gregorich et al. | |
| 8,308,790 B2 | 11/2012 | Arbefeuille et al. | |
| 8,333,800 B2 | 12/2012 | Bruszewski et al. | |
| 8,343,211 B2 | 1/2013 | Gregorich et al. | |
| 8,377,113 B2 | 2/2013 | Hartley et al. | |
| 8,449,595 B2 | 5/2013 | Ouellette et al. | |
| 8,470,018 B2 | 6/2013 | Hartley et al. | |
| 8,480,725 B2 | 7/2013 | Rasmussen et al. | |
| 8,480,728 B2 | 7/2013 | Gregorich et al. | |
| 8,486,129 B2 | 7/2013 | Lautherjung | |
| 8,500,792 B2 | 8/2013 | Berra | |
| 8,506,622 B2 | 8/2013 | Bruszewski et al. | |
| 8,636,788 B2 | 1/2014 | Arbefeuille et al. | |
| 8,641,752 B1 | 2/2014 | Holm et al. | |
| 8,702,786 B2 * | 4/2014 | Roeder | A61F 2/07 |
| | | | 623/1.13 |
| 8,728,148 B2 * | 5/2014 | Roeder | A61F 2/07 |
| | | | 623/1.13 |
| 8,740,963 B2 | 6/2014 | Arbefeuille et al. | |
| 8,795,349 B2 * | 8/2014 | Huser | A61F 2/07 |
| | | | 623/1.13 |
| 8,808,351 B2 | 8/2014 | Osborne | |
| 8,828,074 B2 * | 9/2014 | Xiao | A61F 2/07 |
| | | | 623/1.1 |
| 8,870,939 B2 * | 10/2014 | Roeder | A61F 2/856 |
| | | | 623/1.13 |
| 8,915,955 B2 | 12/2014 | West et al. | |
| 8,915,956 B2 * | 12/2014 | Schaeffer | A61F 2/07 |
| | | | 623/1.13 |
| 8,926,693 B2 | 1/2015 | Duffy et al. | |
| 9,101,455 B2 | 8/2015 | Roeder et al. | |
| 9,101,506 B2 | 8/2015 | Arbefeuille et al. | |
| 9,173,755 B2 | 11/2015 | Berra et al. | |
| 9,198,786 B2 | 12/2015 | Moore et al. | |
| 9,220,617 B2 | 12/2015 | Berra | |
| 9,259,336 B2 | 2/2016 | Schaeffer et al. | |
| 9,320,631 B2 | 4/2016 | Moore et al. | |
| 9,333,104 B2 | 5/2016 | Ouellette et al. | |
| 9,358,142 B2 | 6/2016 | Johnson | |
| 9,364,314 B2 | 6/2016 | Berra et al. | |
| 9,408,734 B2 | 8/2016 | Arbefeuille et al. | |
| 9,408,735 B2 | 8/2016 | Arbefeuille et al. | |
| 9,439,751 B2 | 9/2016 | White et al. | |
| 9,561,124 B2 | 2/2017 | Arbefeuille et al. | |
| 9,592,112 B2 | 3/2017 | Arbefeuille et al. | |
| 9,597,204 B2 * | 3/2017 | Benary | A61F 2/856 |
| 9,655,712 B2 | 5/2017 | Berra et al. | |
| 9,770,322 B2 | 9/2017 | Burkart et al. | |
| 9,827,123 B2 | 11/2017 | Arbefeuille et al. | |
| 9,839,542 B2 | 12/2017 | Bruszewski et al. | |
| 9,861,503 B2 | 1/2018 | Barthold et al. | |
| 9,877,857 B2 | 1/2018 | Arbefeuille et al. | |
| 9,907,686 B2 | 3/2018 | Ouellette et al. | |
| 9,913,743 B2 | 3/2018 | Arbefeuille et al. | |
| 9,925,080 B2 | 3/2018 | Arbefeuille et al. | |
| 10,004,620 B2 | 6/2018 | Treacy et al. | |
| 10,005,269 B2 | 6/2018 | Hall et al. | |
| 10,080,674 B2 | 9/2018 | Yuan et al. | |
| 10,105,248 B2 | 10/2018 | Berra et al. | |
| 10,105,250 B2 | 10/2018 | Berra | |
| 10,182,930 B2 | 1/2019 | Moore et al. | |
| 10,213,291 B2 | 2/2019 | Berra et al. | |
| 10,245,137 B2 | 4/2019 | Scutti et al. | |
| 10,265,202 B2 * | 4/2019 | Greenberg | A61F 2/856 |
| 10,299,951 B2 | 5/2019 | Arbefeuille et al. | |
| 10,307,275 B2 | 6/2019 | Berra et al. | |
| 10,390,930 B2 | 8/2019 | Arbefeuille et al. | |
| 10,478,320 B2 | 11/2019 | Shahriari | |
| 10,485,684 B2 | 11/2019 | Marmur | A61F 2/91 |
| 10,512,556 B2 | 12/2019 | Longo et al. | |
| 10,617,542 B2 | 4/2020 | Chakfe et al. | |
| 10,702,406 B2 | 7/2020 | Swift et al. | |
| 10,744,012 B2 | 8/2020 | Bonsignore et al. | |
| 10,898,357 B2 | 1/2021 | Arbefeuille et al. | |
| 10,987,235 B2 | 4/2021 | Eubanks et al. | |
| 10,987,873 B2 | 4/2021 | Moldave et al. | |
| 11,000,359 B2 | 5/2021 | Torrance et al. | |
| 11,219,540 B2 | 1/2022 | Arbefeuille | |
| 11,278,390 B2 | 3/2022 | Lostetter | |
| 11,291,572 B2 | 4/2022 | Garcia | |
| 11,351,025 B2 | 6/2022 | Lostetter | |
| 11,369,466 B2 * | 6/2022 | Arbefeuille | A61F 2/07 |
| 11,399,929 B2 * | 8/2022 | Arbefeuille | A61F 2/07 |
| 11,413,177 B2 | 8/2022 | Lostetter | |

(56) References Cited

U.S. PATENT DOCUMENTS

| | | | |
|---|---|---|---|
| 11,478,349 B2* | 10/2022 | Torrance | A61F 2/07 |
| 11,547,584 B2 | 1/2023 | Lostetter | |
| 2002/0038144 A1 | 3/2002 | Trout et al. | |
| 2002/0062133 A1 | 5/2002 | Gilson et al. | |
| 2002/0151956 A1 | 10/2002 | Chobotov et al. | |
| 2002/0177890 A1 | 11/2002 | Lenker | |
| 2002/0188344 A1 | 12/2002 | Bolea et al. | |
| 2002/0193872 A1 | 12/2002 | Trout et al. | |
| 2004/0059406 A1 | 3/2004 | Cully et al. | |
| 2004/0073289 A1 | 4/2004 | Hartley | |
| 2004/0138737 A1 | 7/2004 | Davidson et al. | |
| 2005/0102021 A1* | 5/2005 | Osborne | A61F 2/07 623/1.13 |
| 2005/0102023 A1 | 5/2005 | Yadin et al. | |
| 2005/0119722 A1 | 6/2005 | Styrc et al. | |
| 2005/0131517 A1* | 6/2005 | Hartley | A61F 2/07 623/1.13 |
| 2005/0131518 A1* | 6/2005 | Hartley | A61F 2/856 623/1.13 |
| 2005/0131519 A1 | 6/2005 | Hartley | |
| 2005/0131523 A1 | 6/2005 | Bashiri et al. | |
| 2005/0154444 A1 | 7/2005 | Quadri | |
| 2005/0171597 A1 | 8/2005 | Boatman et al. | |
| 2006/0015171 A1 | 1/2006 | Armstrong | |
| 2006/0020319 A1 | 1/2006 | Kim et al. | |
| 2006/0095118 A1 | 5/2006 | Hartley | |
| 2006/0155359 A1 | 7/2006 | Watson | |
| 2006/0184226 A1 | 8/2006 | Austin | |
| 2006/0247760 A1 | 11/2006 | Ganesan et al. | |
| 2006/0247761 A1 | 11/2006 | Greenberg et al. | |
| 2007/0021822 A1* | 1/2007 | Boatman | A61F 2/91 623/1.13 |
| 2007/0055358 A1 | 3/2007 | Krolik et al. | |
| 2007/0055360 A1 | 3/2007 | Hanson et al. | |
| 2007/0067023 A1* | 3/2007 | Kveen | A61F 2/915 623/1.35 |
| 2007/0112418 A1 | 5/2007 | Eidenschink et al. | |
| 2007/0135904 A1* | 6/2007 | Eidenschink | A61F 2/92 623/1.35 |
| 2007/0208414 A1 | 9/2007 | Sorenson et al. | |
| 2007/0208419 A1 | 9/2007 | Meyer et al. | |
| 2007/0213805 A1 | 9/2007 | Schaeffer et al. | |
| 2007/0233223 A1 | 10/2007 | Styrc | |
| 2007/0244542 A1* | 10/2007 | Greenan | A61F 2/07 623/1.13 |
| 2007/0244547 A1* | 10/2007 | Greenan | A61F 2/07 623/1.35 |
| 2007/0250152 A1* | 10/2007 | Xiao | A61F 2/89 623/1.13 |
| 2008/0091260 A1 | 4/2008 | Pomeranz et al. | |
| 2008/0132988 A1 | 6/2008 | Jordan | |
| 2008/0264102 A1 | 10/2008 | Berra | |
| 2008/0281399 A1* | 11/2008 | Hartley | A61F 2/07 623/1.13 |
| 2009/0030502 A1* | 1/2009 | Sun | A61F 2/07 623/1.16 |
| 2009/0043377 A1 | 2/2009 | Greenberg et al. | |
| 2009/0048663 A1 | 2/2009 | Greenberg | |
| 2009/0248135 A1 | 10/2009 | Bruszewski et al. | |
| 2009/0264990 A1 | 10/2009 | Bruszewski et al. | |
| 2010/0004730 A1 | 1/2010 | Benjamin et al. | |
| 2010/0030253 A1* | 2/2010 | Harris | A61F 2/01 606/200 |
| 2010/0057186 A1* | 3/2010 | West | A61F 2/07 623/1.13 |
| 2010/0063576 A1 | 3/2010 | Schaeffer et al. | |
| 2010/0121429 A1 | 5/2010 | Greenan et al. | |
| 2010/0268319 A1 | 10/2010 | Bruszewski et al. | |
| 2010/0316830 A1 | 12/2010 | Hartley et al. | |
| 2011/0077730 A1 | 3/2011 | Fenster | |
| 2011/0190862 A1 | 8/2011 | Bashiri et al. | |
| 2011/0190868 A1* | 8/2011 | Ducke | A61F 2/07 623/1.13 |
| 2011/0257720 A1 | 10/2011 | Peterson et al. | |
| 2011/0319983 A1* | 12/2011 | Zhu | A61F 2/07 623/1.35 |
| 2012/0022630 A1 | 1/2012 | Wubbeling | |
| 2012/0035714 A1 | 2/2012 | Ducke et al. | |
| 2012/0172965 A1 | 7/2012 | Kratzberg et al. | |
| 2012/0191174 A1 | 7/2012 | Vinluan et al. | |
| 2012/0296360 A1 | 11/2012 | Norris et al. | |
| 2013/0116773 A1 | 5/2013 | Roeder et al. | |
| 2013/0116775 A1 | 5/2013 | Roeder et al. | |
| 2013/0123900 A1 | 5/2013 | Eblacas et al. | |
| 2013/0158648 A1 | 6/2013 | Hartley et al. | |
| 2013/0211505 A1 | 8/2013 | Robison | |
| 2013/0282102 A1* | 10/2013 | Peterson | A61F 2/07 623/1.13 |
| 2013/0289696 A1 | 10/2013 | Maggard et al. | |
| 2013/0289713 A1 | 10/2013 | Pearson et al. | |
| 2014/0046428 A1 | 2/2014 | Cragg et al. | |
| 2014/0180378 A1 | 6/2014 | Roeder | |
| 2014/0200651 A1* | 7/2014 | Chuter | A61F 2/07 623/1.13 |
| 2014/0324150 A1 | 10/2014 | Stephens et al. | |
| 2015/0105819 A1 | 4/2015 | Becking et al. | |
| 2015/0105849 A1 | 4/2015 | Cohen et al. | |
| 2015/0105850 A1 | 4/2015 | Shahriari | |
| 2015/0202065 A1 | 7/2015 | Shalev et al. | |
| 2015/0202067 A1 | 7/2015 | Barrand et al. | |
| 2015/0216686 A1 | 8/2015 | Chakfe et al. | |
| 2015/0335452 A1 | 11/2015 | Rao et al. | |
| 2016/0100969 A1 | 4/2016 | Lesmeister et al. | |
| 2016/0106564 A1 | 4/2016 | Roeder et al. | |
| 2016/0120667 A1 | 5/2016 | Bolduc et al. | |
| 2016/0184078 A1 | 6/2016 | Choubey et al. | |
| 2016/0199207 A1 | 7/2016 | Treacy et al. | |
| 2016/0296353 A1 | 10/2016 | Skender | |
| 2016/0302950 A1 | 10/2016 | Marmur et al. | |
| 2017/0281382 A1 | 10/2017 | Lostetter et al. | |
| 2018/0153680 A1 | 6/2018 | Greenberg et al. | |
| 2019/0159886 A1* | 5/2019 | Antonio Lourenco | A61F 2/07 |
| 2019/0231514 A1 | 8/2019 | Arbefeuille | |
| 2019/0231571 A1 | 8/2019 | Lostetter | |
| 2019/0247213 A1 | 8/2019 | Lostetter | |
| 2019/0269497 A1* | 9/2019 | Arbefeuille | A61F 2/95 |
| 2019/0269498 A1 | 9/2019 | Arbefeuille et al. | |
| 2019/0282355 A1* | 9/2019 | Lostetter | A61F 2/07 |
| 2019/0328556 A1* | 10/2019 | Eubanks | A61F 2/06 |
| 2019/0350694 A1 | 11/2019 | Arbefeuille et al. | |
| 2020/0246165 A1 | 8/2020 | Arbefeuille et al. | |
| 2020/0352700 A1 | 11/2020 | Torrance et al. | |
| 2021/0052364 A1* | 2/2021 | Guo | A61F 2/07 |
| 2021/0100669 A1 | 4/2021 | Arbefeuille et al. | |
| 2021/0236262 A1 | 8/2021 | Torrance et al. | |
| 2022/0087841 A1 | 3/2022 | Arbefeuille | |
| 2022/0168091 A1 | 6/2022 | Lostetter | |
| 2022/0257361 A1 | 8/2022 | Lostetter | |
| 2022/0304798 A1 | 9/2022 | Arbefeuille | |
| 2022/0378594 A1 | 12/2022 | Lostetter | |
| 2022/0395365 A1* | 12/2022 | Lostetter | A61F 2/07 |
| 2023/0063108 A1 | 3/2023 | Magen et al. | |
| 2024/0058114 A1 | 2/2024 | Arbefeuille | |

FOREIGN PATENT DOCUMENTS

| | | | | |
|---|---|---|---|---|
| CN | 105832447 A | 8/2016 | | |
| CN | 105943213 A | 9/2016 | | |
| EP | 1673040 A1 | 6/2006 | | |
| EP | 1847234 A1 * | 10/2007 | | A61F 2/07 |
| EP | 2501334 A1 | 9/2012 | | |
| EP | 2517672 A1 | 10/2012 | | |
| EP | 2735283 A1 | 5/2014 | | |
| EP | 2740440 A2 | 6/2014 | | |
| EP | 2745812 A1 | 6/2014 | | |
| EP | 2749250 A1 | 7/2014 | | |
| EP | 2606851 B1 | 11/2015 | | |
| EP | 3040054 A1 | 7/2016 | | |
| EP | 3146993 A1 | 3/2017 | | |
| EP | 3272319 A1 | 1/2018 | | |
| FR | 2932979 A1 | 1/2010 | | |
| JP | 2012/152549 A | 8/2012 | | |
| WO | WO-1997/25002 A1 | 7/1997 | | |

(56) References Cited

FOREIGN PATENT DOCUMENTS

| | | | | |
|---|---|---|---|---|
| WO | WO-99/29262 A1 | 6/1999 | | |
| WO | WO-99/34749 A1 | 7/1999 | | |
| WO | WO-03/099108 A2 | 12/2003 | | |
| WO | WO-2005034809 A1 * | 4/2005 | ............... | A61F 2/07 |
| WO | WO-2005034810 A1 * | 4/2005 | ............... | A61F 2/07 |
| WO | WO-2006/037086 A1 | 4/2006 | | |
| WO | WO-2006036690 A1 * | 4/2006 | ............... | A61F 2/07 |
| WO | WO-2009/148594 A1 | 12/2009 | | |
| WO | WO-2010/024880 A1 | 3/2010 | | |
| WO | WO-2010/030370 A1 | 3/2010 | | |
| WO | WO-2010/127040 A1 | 11/2010 | | |
| WO | WO-2012/047308 A1 | 4/2012 | | |
| WO | WO-2012/116368 A2 | 8/2012 | | |
| WO | WO-2012/145823 A1 | 11/2012 | | |
| WO | WO-2014/162306 A2 | 10/2014 | | |
| WO | WO-2015/059019 A1 | 4/2015 | | |
| WO | WO-2015/070792 A1 | 5/2015 | | |
| WO | WO-2016/122862 A1 | 8/2016 | | |
| WO | WO-2017/072168 A1 | 5/2017 | | |
| WO | WO-2017218474 A1 * | 12/2017 | ............... | A61F 2/06 |
| WO | WO-2018/026768 A1 | 2/2018 | | |
| WO | WO-2018/156849 A1 | 8/2018 | | |
| WO | WO-2018/156850 A1 | 8/2018 | | |
| WO | WO-2018156848 A1 * | 8/2018 | ............... | A61F 2/07 |
| WO | WO-2022/265985 A1 | 12/2022 | | |
| WO | WO-2022/265989 A1 | 12/2022 | | |
| WO | WO-2022/0265989 A8 | 12/2022 | | |

OTHER PUBLICATIONS

International Preliminary Report on Patentability for International Application No. PCT/US2018/019350 dated Aug. 27, 2019.

Luo et al., "Stent-grafts for the treatment of TIPS dysfunction: Fluency stent vs. Wallgrent stent," World J Gastroenterol, 19(30): 5000-5005 (2013).

Wang et al. "Preliminary experimental study on a novel adjustable sutureless aortic prosthesis" Chinese Journal of Experimental Surgery, 23(11): 1325-1327 w/ English Abstract (2006).

International Search Report and Written Opinion for International Application No. PCT/US22/33247 dated Sep. 13, 2022.

International Search Report and Written Opinion for Application No. PCT/US2022/033239 Nov. 7, 2022.

* cited by examiner

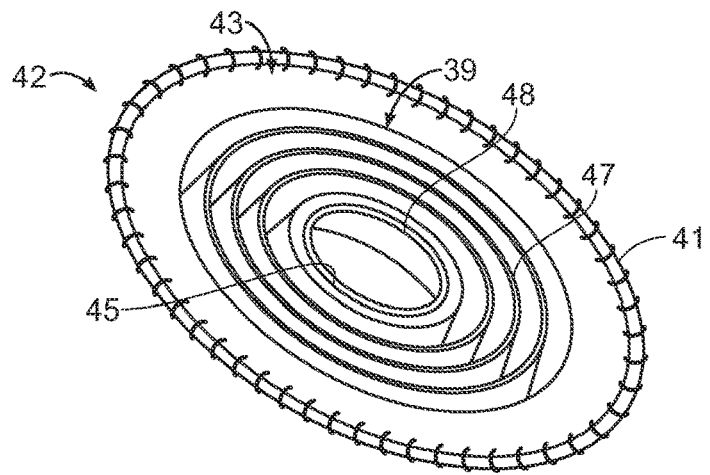
FIG. 2
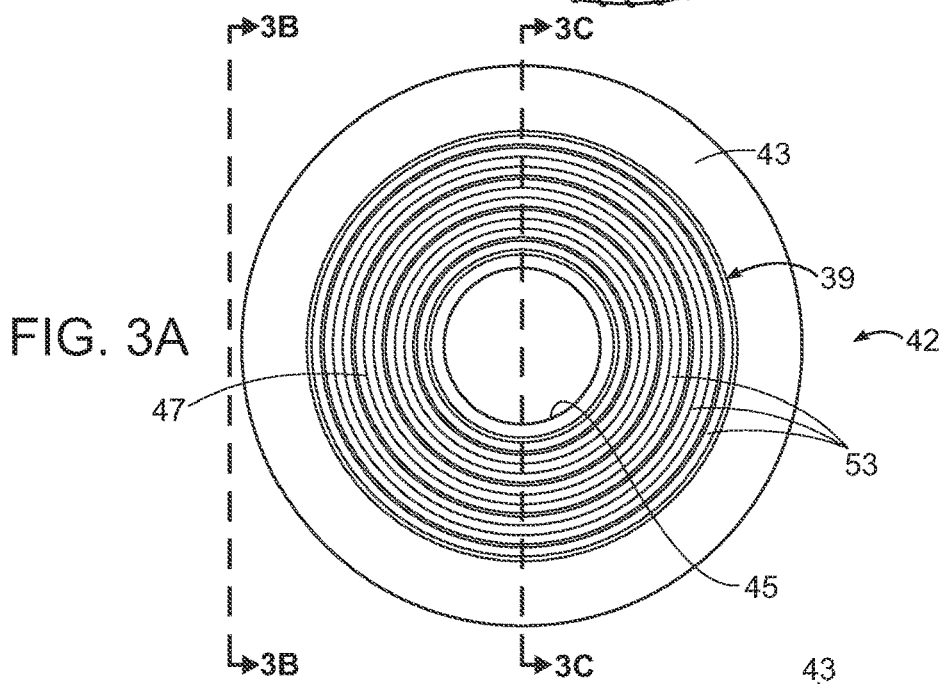
FIG. 3A
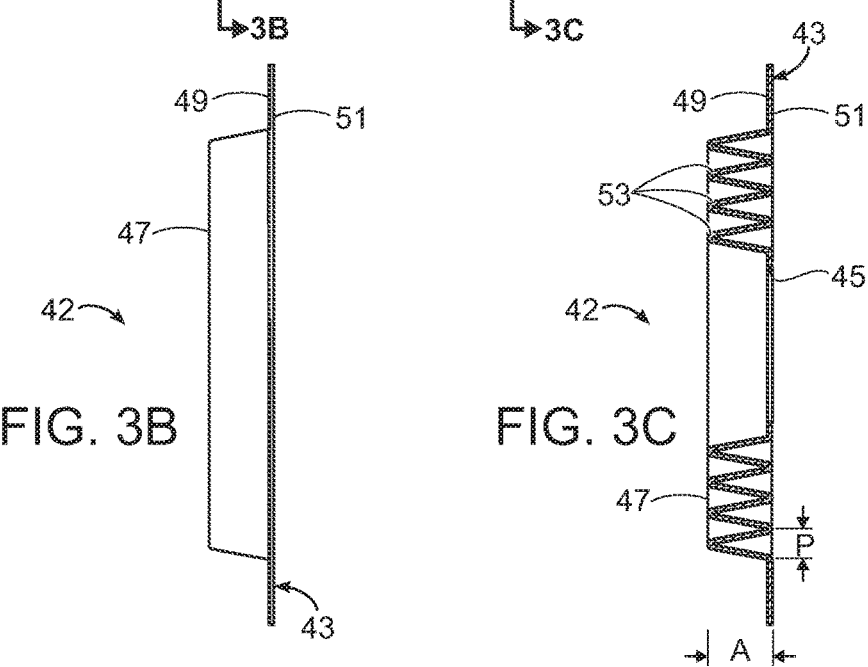
FIG. 3B
FIG. 3C

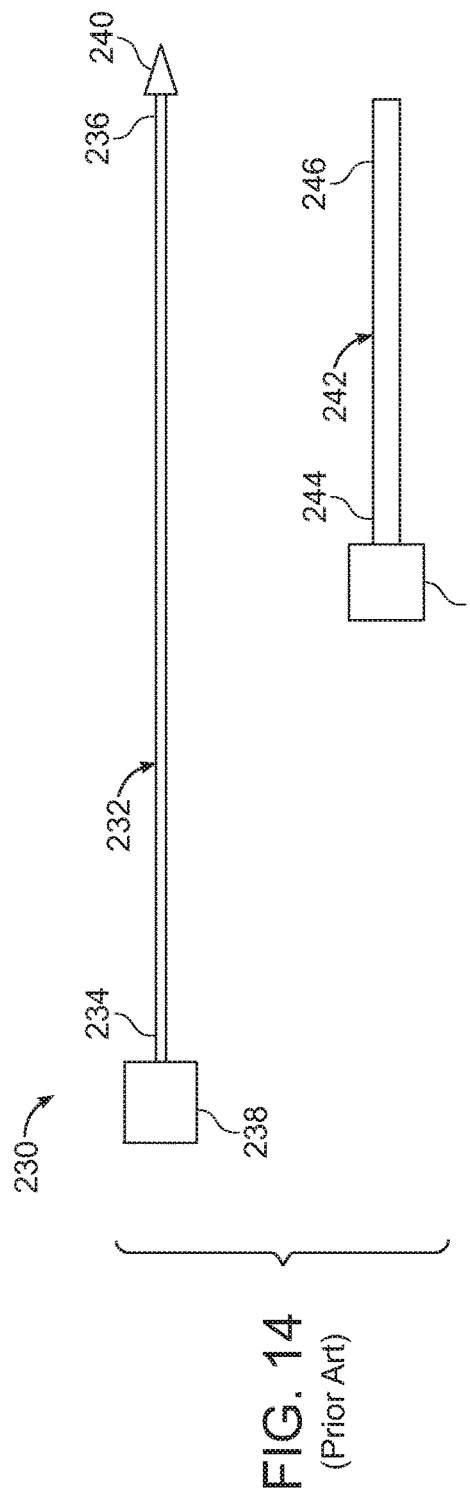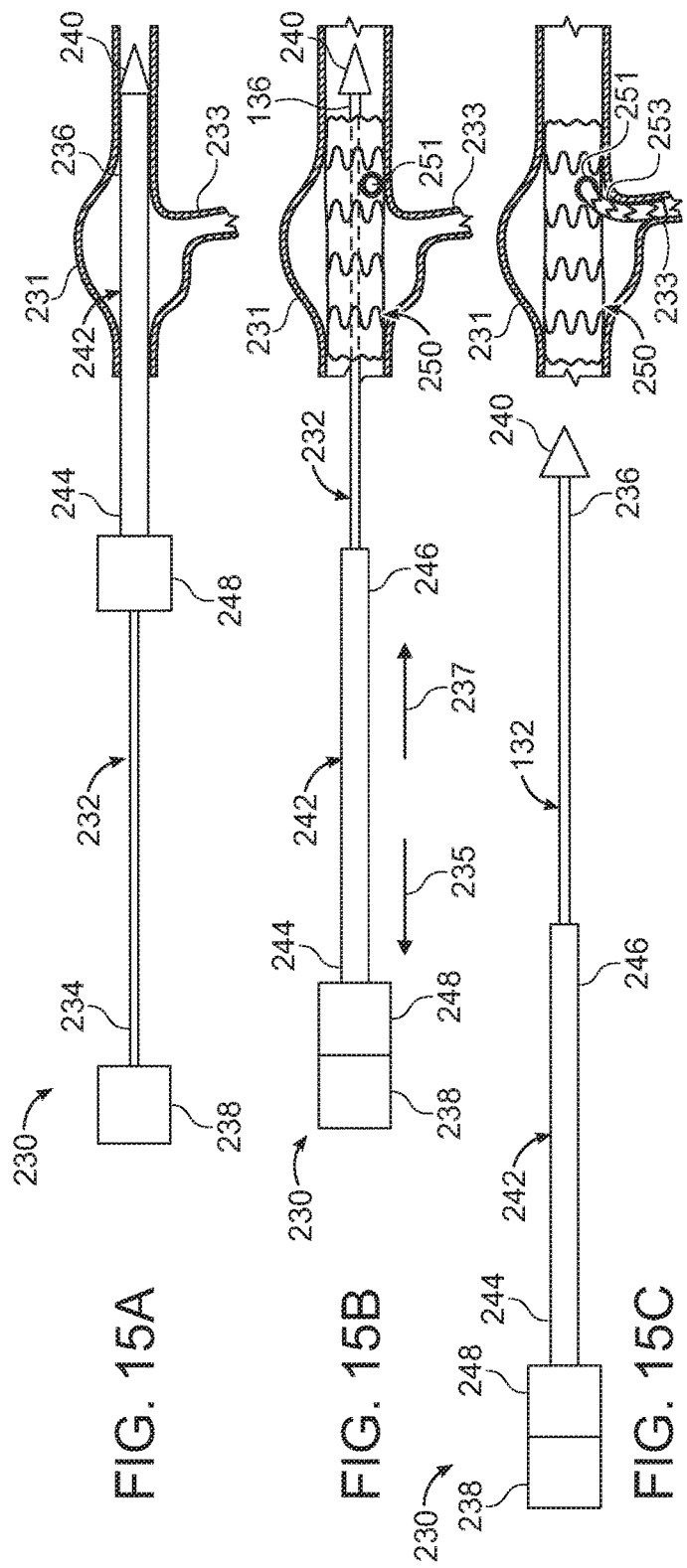
FIG. 14 (Prior Art)
FIG. 15A
FIG. 15B
FIG. 15C

VASCULAR PROSTHESIS WITH CRIMPED ADAPTER AND METHODS OF USE

RELATED APPLICATIONS

This application is a Continuation of U.S. application Ser. No. 17/848,921, filed on Jun. 24, 2022, which is a division of U.S. application Ser. No. 16/414,208, filed May 16, 2019, which is a continuation of International Application No. PCT/US2018/019350, which designated the United States and was filed on Feb. 23, 2018, published in English, which claims the benefit of U.S. Provisional Application No. 62/463,063, filed on Feb. 24, 2017. The entire teachings of the above applications are incorporated herein by reference.

BACKGROUND

Fenestrated endovascular aortic repair (FEVAR) is a minimally invasive procedure to treat aortic aneurysms that span blood vessels arising from the aorta that supply blood to vital organs including the kidneys, intestine and liver. Endovascular grafts employed in FEVAR define fenestrations for insertion of branch prostheses that serve as passageways for blood flow through arterial branches to vital organs following implantation of the endovascular graft. Maximizing blood flow to vital organs and minimizing endoleaks following repair of aneurysms with fenestrated vascular prostheses, such as juxtarenal aortic aneurysms and short-neck abdominal aortic aneurysms, present medical challenges that must be overcome or minimized if additional surgical intervention is to be avoided.

Therefore, a need exits for new and improved endovascular repair devices and methods of their use to treat arterial pathologies, such as juxtarenal and short-neck abdominal aortic aneurysms.

SUMMARY

The present invention relates to vascular prostheses for use in treating and repairing arterial vascular damage, such as vascular damage associated with an aortic aneurysm in regions of the aorta having arterial branches to vital organs and tissues, such as juxtarenal aortic aneurysms and short-neck abdominal aortic aneurysms.

In one embodiment, the invention is a vascular prosthesis that includes a luminal graft component and a crimped adapter. The luminal graft component includes a proximal open end, a distal open end, and defines a main lumen extending from the proximal open end to the distal open end, the luminal graft component defining at least one fenestration. The crimped adapter at the at least one fenestration includes a perimeter region that is fixed to the luminal graft component and seals the fenestration. The crimped adapter also defines an opening with a diameter smaller than the diameter of the fenestration. The crimped adapter includes a crimped portion having generally concentric folds within the perimeter section and about the opening, whereby the crimped adapters can adapt to positioning of a branch prosthesis extending through the opening by flexation of the folds to thereby move the opening relative to the perimeter region.

In an additional embodiment, the invention is a vascular prosthesis that includes a luminal graft component having a proximal open end, a distal open end, and defining a main lumen extending from the proximal open end to the distal open end. The luminal graft component includes concentric crimped folds about a fenestration defined by the luminal graft component, whereby the concentric crimped folds defining the fenestration can move relative to the remainder of the graft component.

In a further embodiment, the invention is a method for treating an aortic aneurysm that includes delivering a vascular prosthesis through an aorta to an aortic aneurysm of a patient. The vascular prosthesis is radially and releasably constricted and includes a luminal graft component having a proximal open end, distal open end, and a main lumen extending from the proximal open end to the distal open end. The luminal graft component also defines at least one fenestration. A crimped adapter of the vascular prosthesis is fixed at the fenestration and includes a perimeter region that seals the fenestration. The crimped adapter also defines an opening with a diameter smaller than that of a diameter of the fenestration and includes a crimped portion of generally concentric folds within the perimeter section and about the opening, whereby the crimped adapter can adapt to positioning of a branch prosthesis extending through the opening by flexation of the folds to thereby move the opening relative to the perimeter region. The opening of the crimped adapter is substantially aligned with at least one arterial branch at the arterial aneurysm of the patient. The vascular prosthesis is at least partially released from radial constriction. At least one radially and releasably constricted branch prosthesis is delivered through the proximal open end or the distal open end of the luminal graft component of the vascular prosthesis and into the main luminal of the luminal graft component. The branch prosthesis is then directed through the opening of the crimped adapter and the fenestration of the luminal graft component, and a distal end of each branch prosthesis is directed into a corresponding arterial branch. The proximal end of the branch prosthesis is secured by the opening of the crimped adapter. Each branch prosthesis is released from radial constriction, thereby treating the aortic aneurysm.

The vascular prostheses of the invention have several advantages by, for example, providing the surgeon with increased flexibility to accommodate anatomical variations in the size and position of arterial branches at an aneurysm. The vascular prostheses of the invention have the additional advantage of improving alignment between the fenestration of the vascular prosthesis of the invention and a branch prosthesis following insertion of the branch prosthesis into the fenestration, thereby significantly reducing the incidence and severity of endoleaks and associated complications.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments. The same number in different drawings indicated the same item.

FIG. 2 is a perspective view of one embodiment of a crimped adapter of the vascular prosthesis shown in FIG. 1.

FIG. 3A is a plan view of the crimped adapter of FIG. 2.

FIG. 3B is a side view of the crimped adapter of FIG. 3A as seen along line 3B-3B of FIG. 3A.

FIG. 3C is a cross-sectional view of the crimped adapter of FIG. 3A taken along line 3C-3C.

FIG. 14 is an exploded view of one embodiment of a prior art delivery device suitable for use with the invention.

FIG. 15A is a side view of the prior art delivery device shown in FIG. 14, and containing a vascular prosthesis of the invention (not shown) loaded within an introducer sheath of the prior art delivery system.

FIG. 15B is a side view of the delivery device shown in FIG. 15A after retraction of the introducer sheath of the delivery device to expose a vascular prosthesis of the invention or a branch prosthesis during delivery to an aneurysm site.

FIG. 15C is a side view of the delivery device shown in FIGS. 15A and 15B after retraction of the delivery device from the vascular prosthesis of the invention or the branch prosthesis, thereby completing implantation of the prosthesis and treatment of an aneurysm site in a patient.

DETAILED DESCRIPTION

The invention is generally directed to vascular prostheses for use in treating and repairing aortic vascular damage, such as vascular damage associated with an aortic aneurysm in regions of the aorta having arterial branches to vital organs and tissues, such as juxtarenal aortic aneurysms and short-neck abdominal aortic aneurysms.

The features and other details of the invention, either as steps of the invention or as combinations of parts of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

A description of example embodiments of the invention follows.

When reference is made herein to a prosthesis, also referred to herein as "stent graft," "stent graft prosthesis," or "vascular prosthesis," to be delivered, or implanted in a patient, the word "proximal" means that portion of the prosthesis or component of the prosthesis that is relatively close to the heart of the patient and "distal" means that portion of the prosthesis or component of the prosthesis that is relatively far from the heart of the patient. A "longitudinal axis," as that term is defined herein, means an axis along a lengthwise direction of a body that also passes through a center of gravity of the body.

When, however, reference is made to a delivery system or a component of a delivery system employed to deliver, or implant, a prosthesis, the word, "proximal," as employed herein, means closer to the clinician using the delivery system. When reference is made to a delivery system or a component of a delivery system, "distal," as that term is employed herein, means, further away from the clinician using the delivery system.

For clarity, the word "proximate" means "close to," as opposed to the meanings ascribed to "proximal" or "distal" described above with respect to either the prosthesis or a delivery system.

Figure 1:
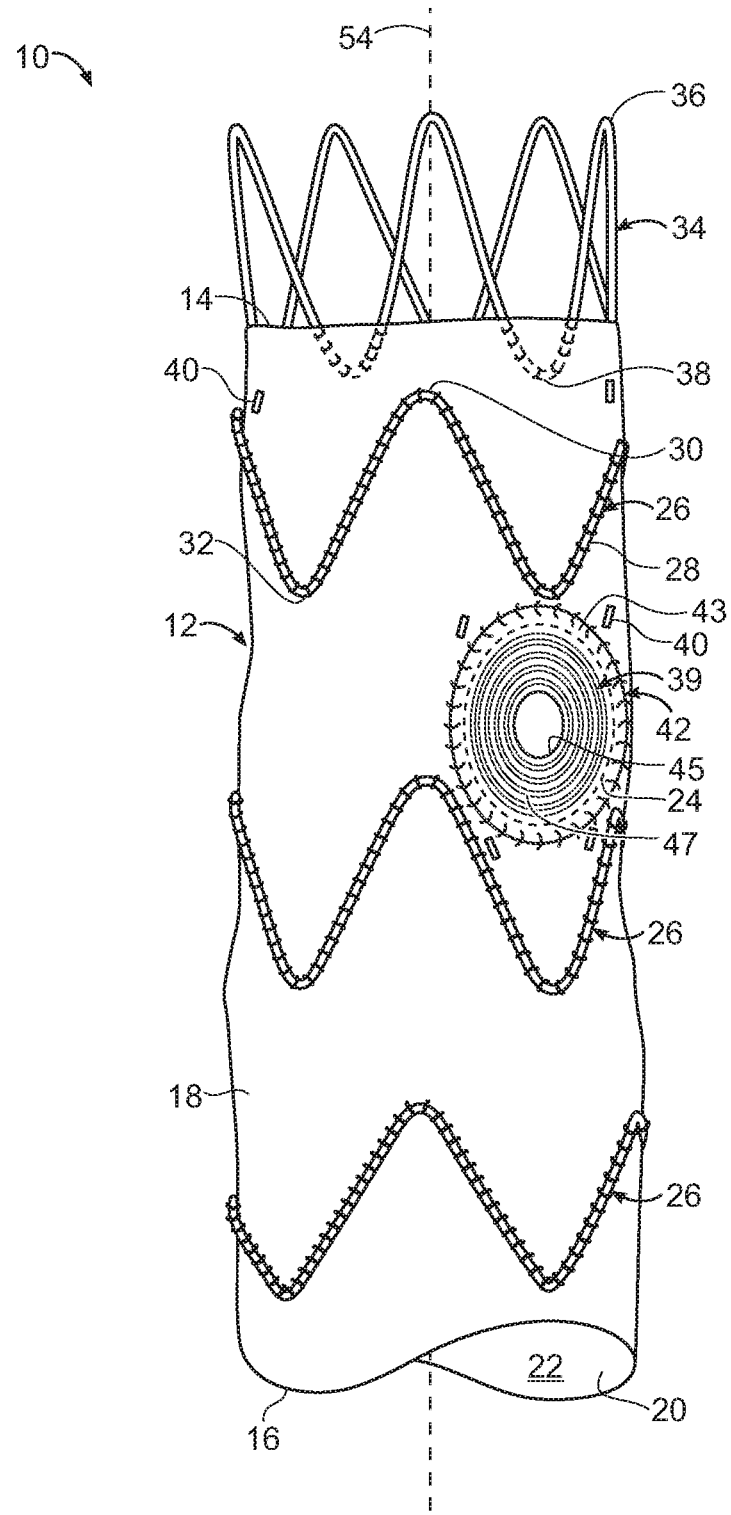
FIG. 1 is a side view of one embodiment of a vascular prosthesis of the invention.

One embodiment of the vascular prosthesis of the invention is shown in FIG. 1. As shown therein, vascular prosthesis 10 includes luminal graft component 12 having proximal open end 14, distal open end 16, outside surface 18, and inside surface 20. Inside surface 20 defines main lumen 22 extending from proximal open end 14 to distal open end 16. Luminal graft component 12 defines fenestration 24 and is formed of a suitable material, such as are known to those skilled in the art, including, for example, at least one member of the group consisting of expanded polytetrafluoroethylene (PTFE), such as ePTFE, and polyethylene terephthalate (PET), such as woven polyester.

Stents 26 extend longitudinally along outside surface 18 of luminal graft component 12, and include struts 28 that join at opposite ends to define proximal apices 30 and distal apices 32. Bare stent 34 at proximal end 14 includes proximal apices 36 and distal apices 38, and is fixed to inside surface 20 of luminal graft component 12 at distal apices 38. Stents 28 and bare stent 34 are formed of a suitable material known to those skilled in the art, such as Nitinol or some other suitable shape memory alloy. Optionally, radiopaque markers 40, such as are known to those skilled in the art, are secured by, for example, suturing or employing a biocompatible adhesive to luminal graft component 12 and about a periphery of fenestration 24.

Crimped adapter 42 encompasses fenestration 24 and is fixed to luminal graft component 12 and is sealed with luminal graft component 12 at fenestration 24. Crimped adapter 42 is formed of a suitable material, such as at least one member of the group consisting of expanded polytetrafluoroethylene (PTFE), such as ePTFE, and polyethylene terephthalate (PET), such as woven polyester, polymers, silicone. Crimped adapter 42 is fixed to and forms a seal with luminal graft component 12 about fenestration 24 by a suitable technique, such as a technique known to those skilled in the art, including, for example, use of sutures, or by using a suitable biocompatible adhesive. In an embodiment, crimped adapter 42, stents 28 and radiopaque markers 40 include radiopaque materials, such as at least one radiopacifier selected from the group consisting of barium sulfate, bismuth, tungsten, platinum, platinum-iridium, tantalum and tantalum-tungsten.

FIG. 2 is a perspective view of crimped adapter 42 of vascular prosthesis 10 of the invention shown in FIG. 1. As shown therein, crimped adapter 42 includes perimeter section 43. Crimped adapter 42 also defines opening 45.

FIG. 3A is a plan view of crimped adapter 42 of FIG. 2. Concentric folds 53 of crimped portion 47 have an amplitude and periodicity. Crimped portion 47 of crimped adapter 42 includes folds 53 within perimeter section 43 and arranged concentrically about opening 45. FIG. 3B is a side view of crimped adapter 42 of FIG. 3A taken along line 3B-3B, and shows perimeter section 43 of crimped adapter 42 and crimped portion 47. Perimeter section 43 includes first surface 49 and second surface 51. As can be seen in FIG. 3B, crimped portion 47 is raised from first surface 49. Typically, when fixed to a luminal graft component of a vascular prosthesis of the invention, first surface 49 faces the outside surface of the luminal graft component, such as outside surface 18 of luminal graft component 12 shown in FIG. 1. It is to be understood, however, that, alternatively, perimeter section 43 can be fixed to outside section 18 of luminal graft component 12 at second surface 51. It is also to be understood that either first surface 49 or second surface 51 can, instead, be fixed to inside surface 20 of luminal graft component 12. Further, in other embodiments, (not shown), folds of the crimped portion 47 can be raised from both sides relative to surfaces 49 and 51 of perimeter section 43 of crimped adapter 42.

Figure 11:
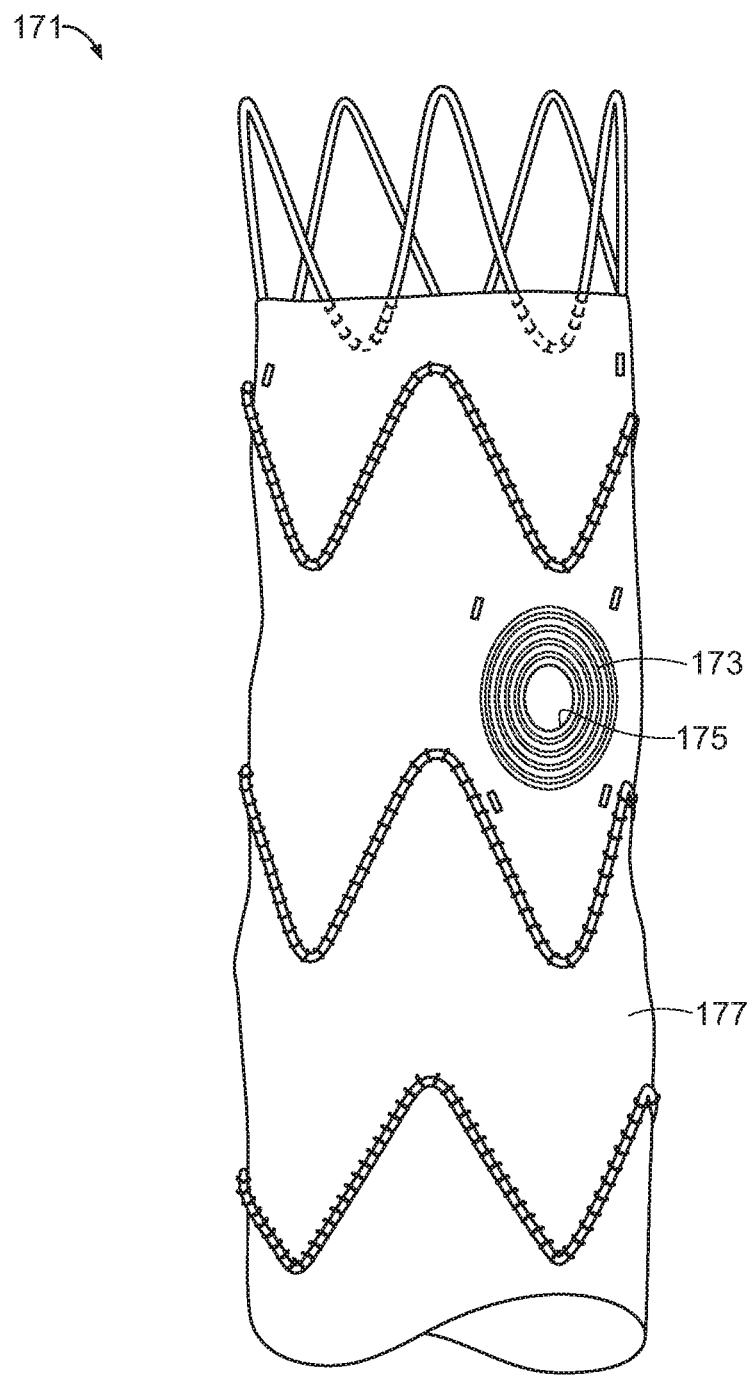
FIG. 11 is a side view of another embodiment of a vascular prosthesis of the invention that includes concentric crimped folds of a luminal graft component about the fenestration defined by a luminal graft component of the vascular prosthesis.

FIG. 3C is a cross sectional view of crimped adapter of FIG. 3A taken along line 3C-3C, showing amplitude A of period P of folds 53 between perimeter section 43 and opening 45. Amplitude A, in an embodiment, is in a range of between about 1 mm and about 10 mm or between about 1 mm and about 5 mm. Also, in an embodiment, period P is in a range of between about 1 mm and about 5 mm, or between about 2 mm and about 4 mm. In an embodiment, the overall diameter of crimped adapter 42 is in a range of between about 10 mm to about 25 mm. In another embodiment, the diameter of opening 45 of crimped adapter 42 is in a range of between about 4 mm to about 14 mm. In an embodiment, crimped adapter 42 includes between about 3 fold to about 10 folds. Although not shown, it is to be understood that, crimped portion 47 of crimped adapter 42 can be circular, oval, round, rectangular, elliptical or some other suitable shape. In one embodiment, shown in FIG. 2, ring 41 is affixed to circumference of perimeter section 43 of crimped adapter 42 or about concentric crimped folds about a fenestration defined by the luminal graft component of the vascular prosthesis, as shown in FIG. 11. Optionally, and is also shown in FIG. 2, ring 48 is affixed to perimeter of opening 45. Ring 41 and ring 48 can be affixed to crimped adapter 42 by, for example, suturing or employing a biocompatible adhesive to crimped adapter 42 about periphery or opening 45.

Referring back to FIG. 1, proximal apices 30 of stents 26 immediately proximal and distal to fenestration 24 of luminal graft component 12 are substantially longitudinally aligned, parallel to longitudinal axis 54, and distal apices 32 of stents 26 immediately proximal and distal to fenestration 24 of luminal graft are also longitudinally aligned parallel to longitudinal axis 54, whereby a general wave-form created by proximal apices 30 of immediately proximal and immediately distal stents 26 are substantially in-phase.

Figure 4:
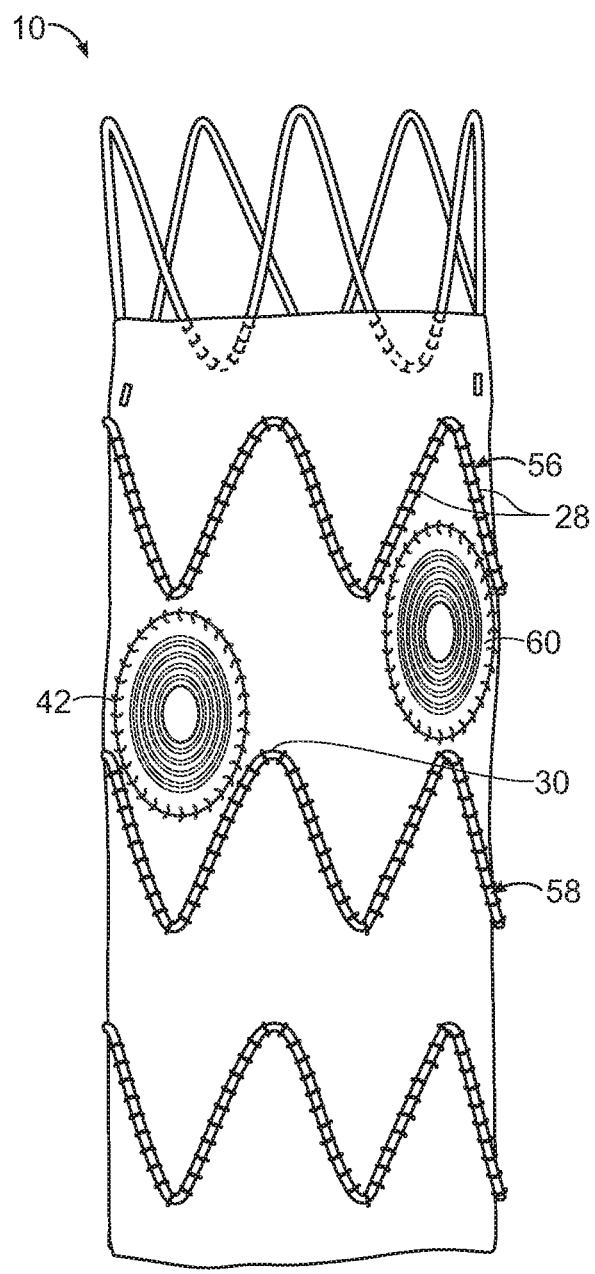
FIG. 4 is a side view of another embodiment of vascular prosthesis of the invention, including two fenestrations and two corresponding crimped adapters that are not positioned laterally relative to each other, wherein one crimped adapter is distal to a distal apex of a stent immediately proximal to the crimped adapter and nested between struts of a stent immediately distal to the crimped adapter, and the other crimped adapter is nested between struts of the stent immediately proximal to the crimped adapter and proximal to a proximal apex of the stent immediately distal to the crimped adapter.

In this embodiment, crimped adapter 42 lies distal to distal apices 32 of immediately proximal stent 56 and are nested between struts 28 of immediately distal stent 58. It is to be understood that multiple fenestrations and associated crimped adapters can be similarly disposed in alternative embodiments of vascular prosthesis 10. For example, as shown in FIG. 4, an additional or alternative crimped adapter 60 can be nested between struts 28 of immediately proximal stent 56 and proximal to proximal apices 30 of immediately distal stent 58. Likewise, additional or alternative fenestrations and crimped adapters can be located in the same or similar arrangements between struts and apices of proximal stent 56 and bare stent 34.

Figure 5:
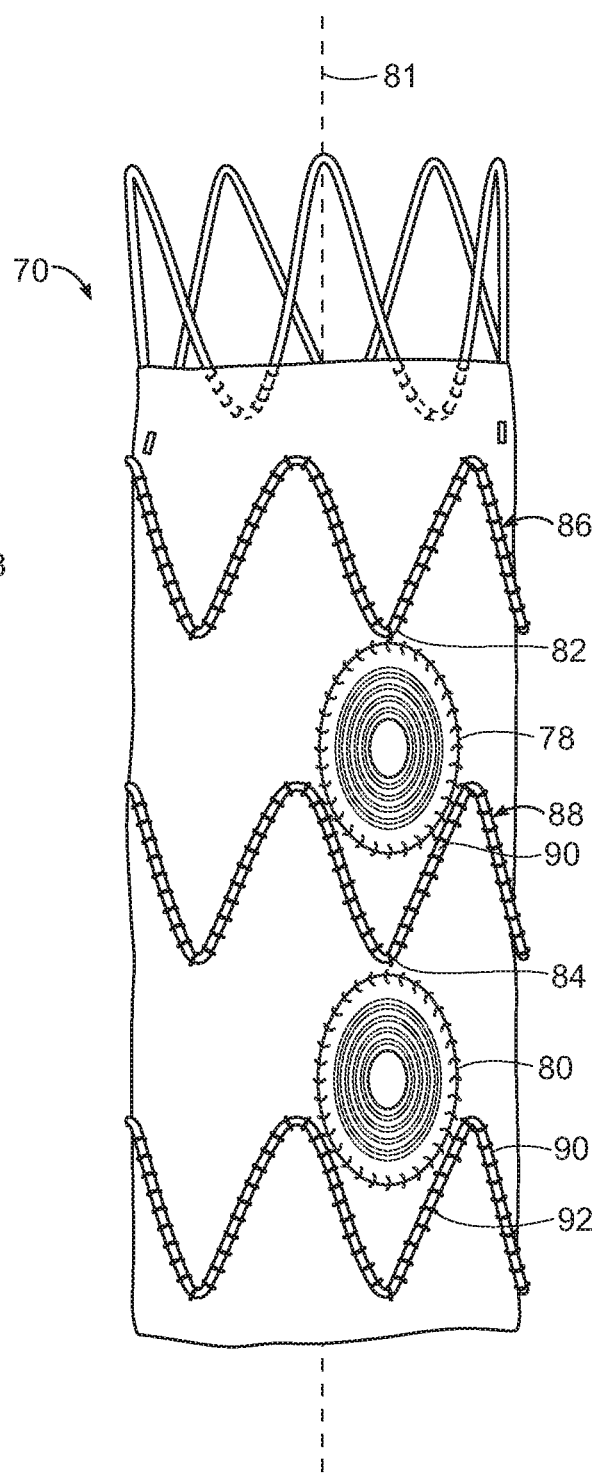
FIG. 5 is a side view of yet another embodiment of the vascular prosthesis of the invention, including two fenestrations and two corresponding crimped adapters, wherein the fenestrations are longitudinally aligned along the longitudinal axis of the vascular prosthesis, and wherein each fenestration associated with each crimped adapter is distal to a distal apex of a stent immediately proximal to the fenestration and nested between struts of a stent immediately distal to the fenestration.

In still another embodiment, a plurality of fenestrations and associated crimped adapters can be aligned longitudinally along a vascular prosthesis of the invention. For example, FIG. 5 is an embodiment of the invention wherein vascular prosthesis 70 includes fenestrations and associated crimped adapters 78, 80, respectively, that are aligned along longitudinal axis 81. In this embodiment, fenestrations and associated crimped adapters 78, 80, respectively, lie distal to distal apices 82, 84 of immediately proximal stent 86, 88, and are nested between struts 90, 92 of stents 88, 90, respectively.

Figure 6:
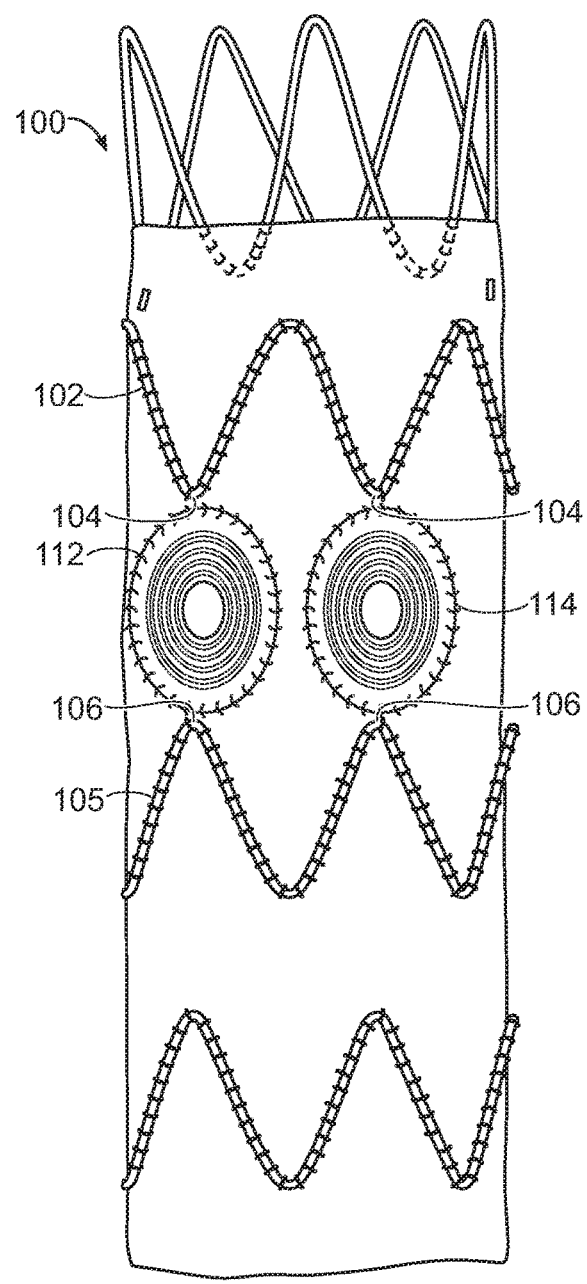
FIG. 6 is a side view of still another embodiment of the vascular prosthesis of the invention, including two fenestrations and two corresponding crimped adapters, wherein the fenestrations are positioned laterally relative to each other and are distal to distal apices of an immediately proximal stent and proximal to proximal apices of an immediately distal stent.
Figure 7:
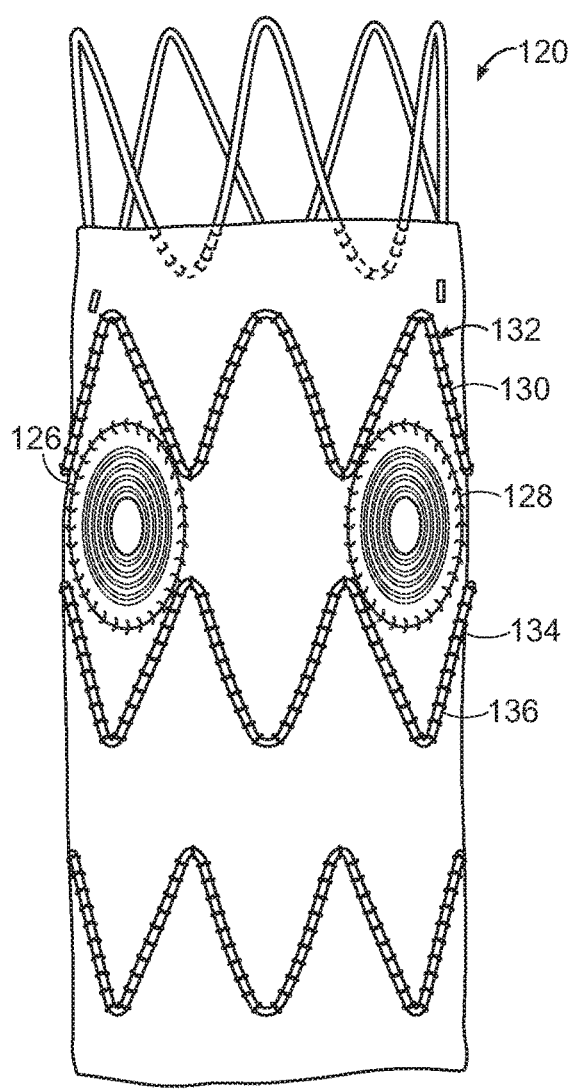
FIG. 7 is a side view of another embodiment of a vascular prosthesis of the invention, including two fenestrations and two corresponding crimped adapters, wherein the fenestrations are positioned laterally relative to each other and are nested between struts of stents immediately proximal and immediately distal to the fenestration.
Figure 8:
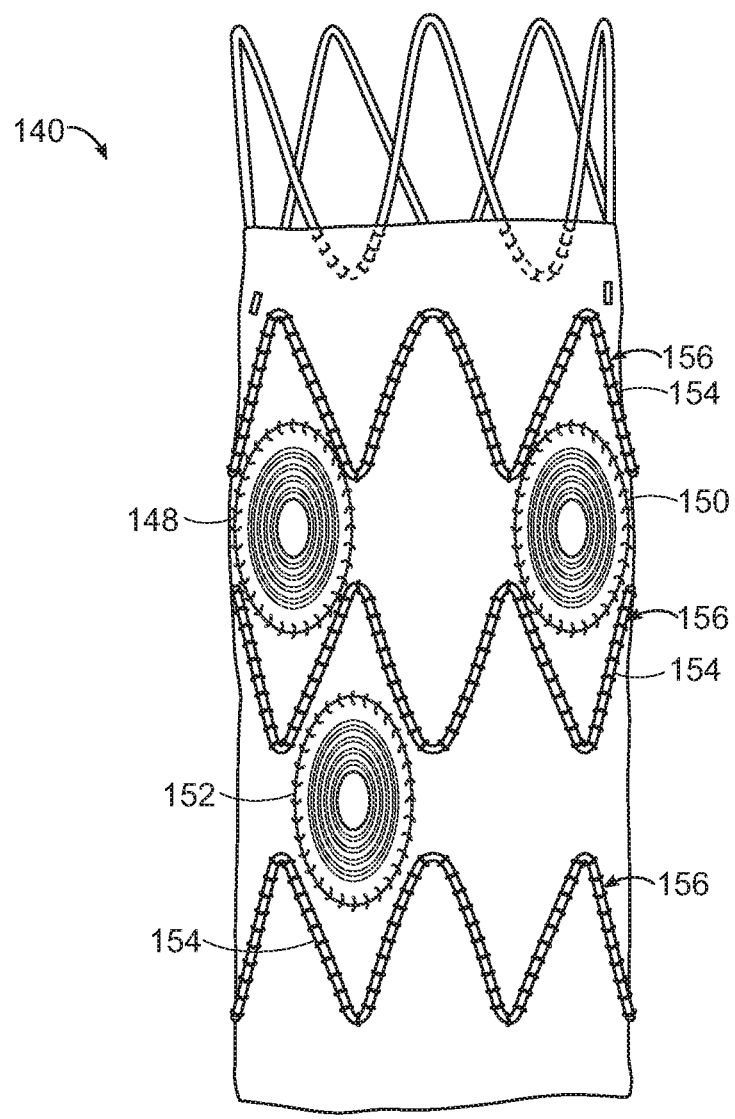
FIG. 8 is a side view of another embodiment of a vascular prosthesis of the invention, including three fenestrations and three corresponding crimped adapters, wherein two of the fenestrations are aligned neither laterally nor longitudinally relative to each other, and wherein all fenestrations are nested between struts of immediately proximal and immediately distal stents.

FIG. 6 is another embodiment of a vascular prosthesis of the invention. As shown therein, vascular prosthesis 100 include stents 102, 105. Stent 102 includes distal apices 104 and stent 105 includes proximate apices 106 that are longitudinally aligned. Fenestrations and associated crimped adapters 112, 114 of the embodiment shown lie between distal apices 104 of immediately proximal stent 102 and immediately proximal to proximal apices 106 of stent 105 immediately distal to fenestrations respectively. In yet another embodiment, shown in FIG. 7, vascular prosthesis 120 includes fenestrations and associated crimped adapters 126, 128 that are arranged laterally and nested between struts 130 of immediately proximal stent 132 and struts 134 of immediately distal stent 136. In still another embodiment, shown in FIG. 8, vascular prosthesis 140 includes fenestrations and associated crimped adapters 148, 150, 152, respectively, not all of which are longitudinally aligned or laterally aligned relative to each other, and lie nested between struts 154 of immediately proximal and distal stents 156. It is to be understood that different combinations of the arrangements identified in FIGS. 1, and 4 through 8, are also various embodiments of the vascular prosthesis of the invention. It is also to be understood that fenestrations and associated crimped adapters of embodiments can be arranged independently of the position of any stent component of the vascular prosthesis of the invention.

Figure 9:
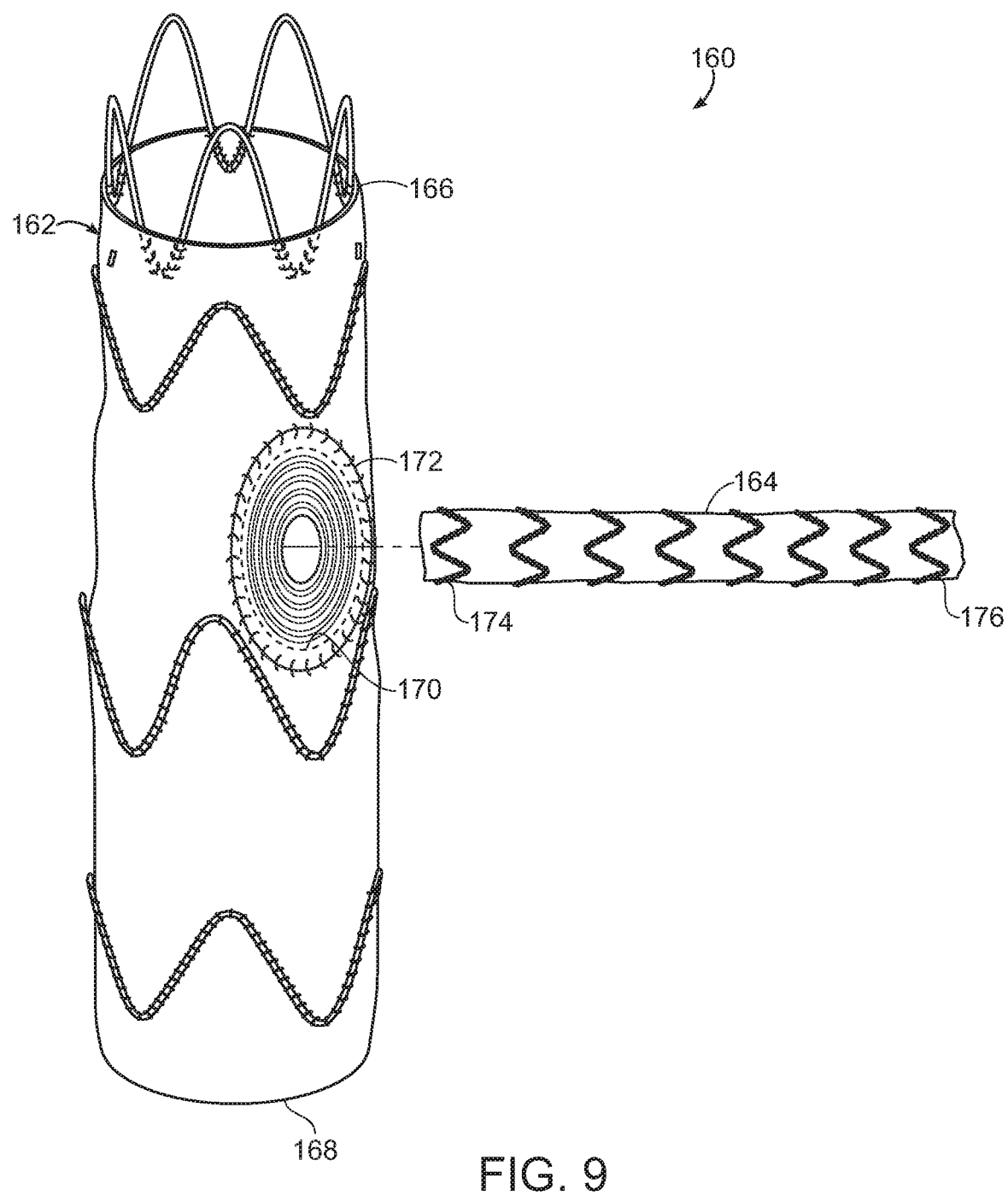
FIG. 9 is an exploded view of a combination of a vascular prosthesis of the invention and a branch prosthesis suitable for use with the vascular prosthesis of the invention.
Figure 10:
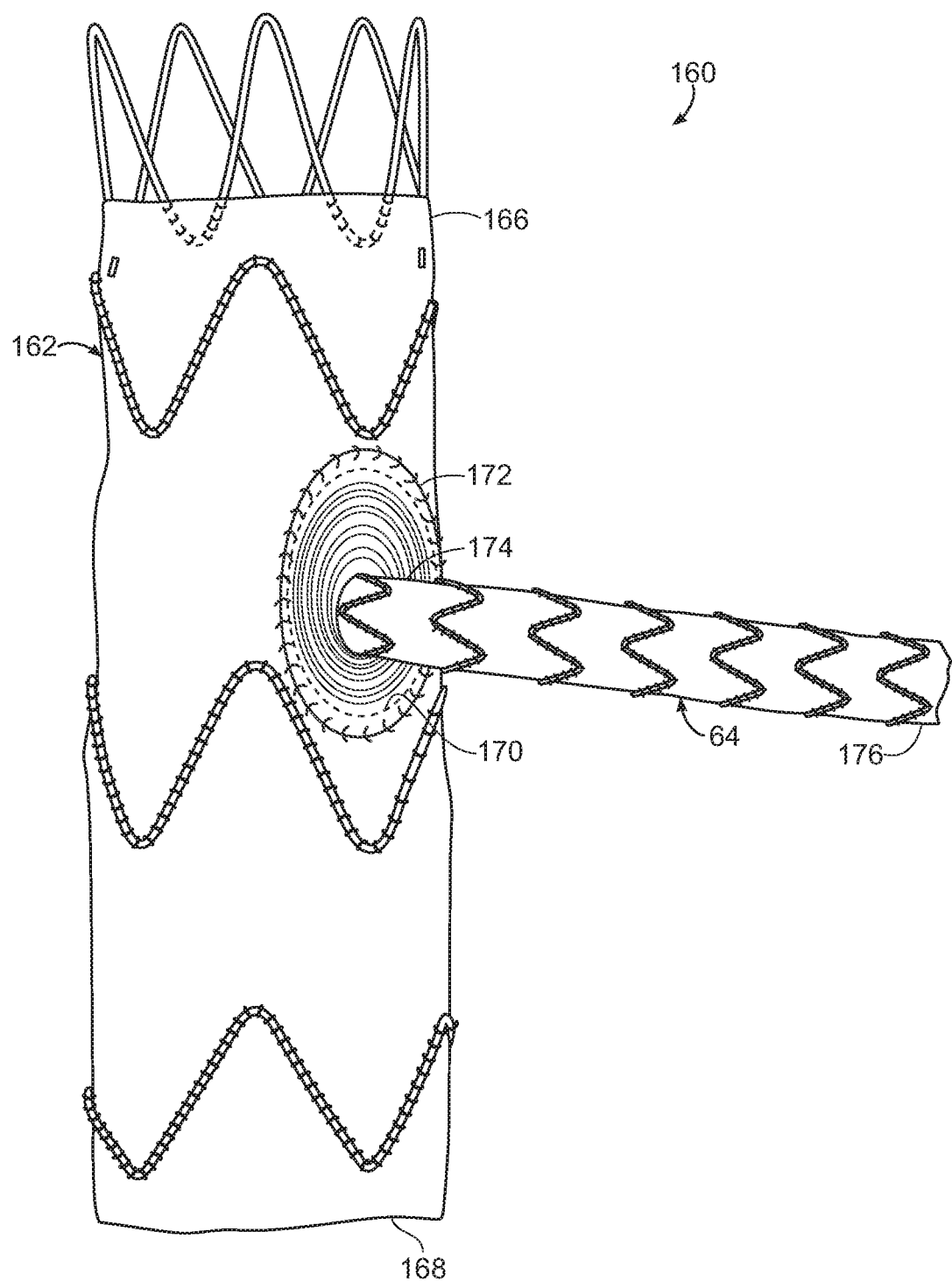
FIG. 10 is an assembled view of the combination shown in FIG. 9.

FIG. 9 is an exploded view of an embodiment of a vascular prosthesis assembly 160 of the invention. As shown therein, vascular prosthesis assembly 160 includes vascular prosthesis main body 162 and least one branch prosthesis 164. Vascular prosthesis main body 162 includes proximal end 166 and distal end 168, and defines fenestration 170 that is encompassed by crimped adapter 172. Branch prosthesis 164 includes proximal end 174 and distal end 176. When assembled, branch prosthesis 164 extends through fenestration 170 and expanded crimped adapter 172, as shown in FIG. 10.

It is to be understood that vascular prosthesis of the invention can include fenestrations having crimped adapters in combination with fenestrations that are not mated with crimped adapters (not shown).

FIG. 11 is a side view of another embodiment of vascular prosthesis 171 of the invention that includes concentric crimped folds 173 about fenestration 175, wherein folds 173 are formed from and as part of luminal graft component 177. Crimped folds 173 define fenestration 175 and move relative to the remainder of luminal graft component 177 in response to positioning of a branch prosthesis (not shown) extending through fenestration 175.

Figure 12:
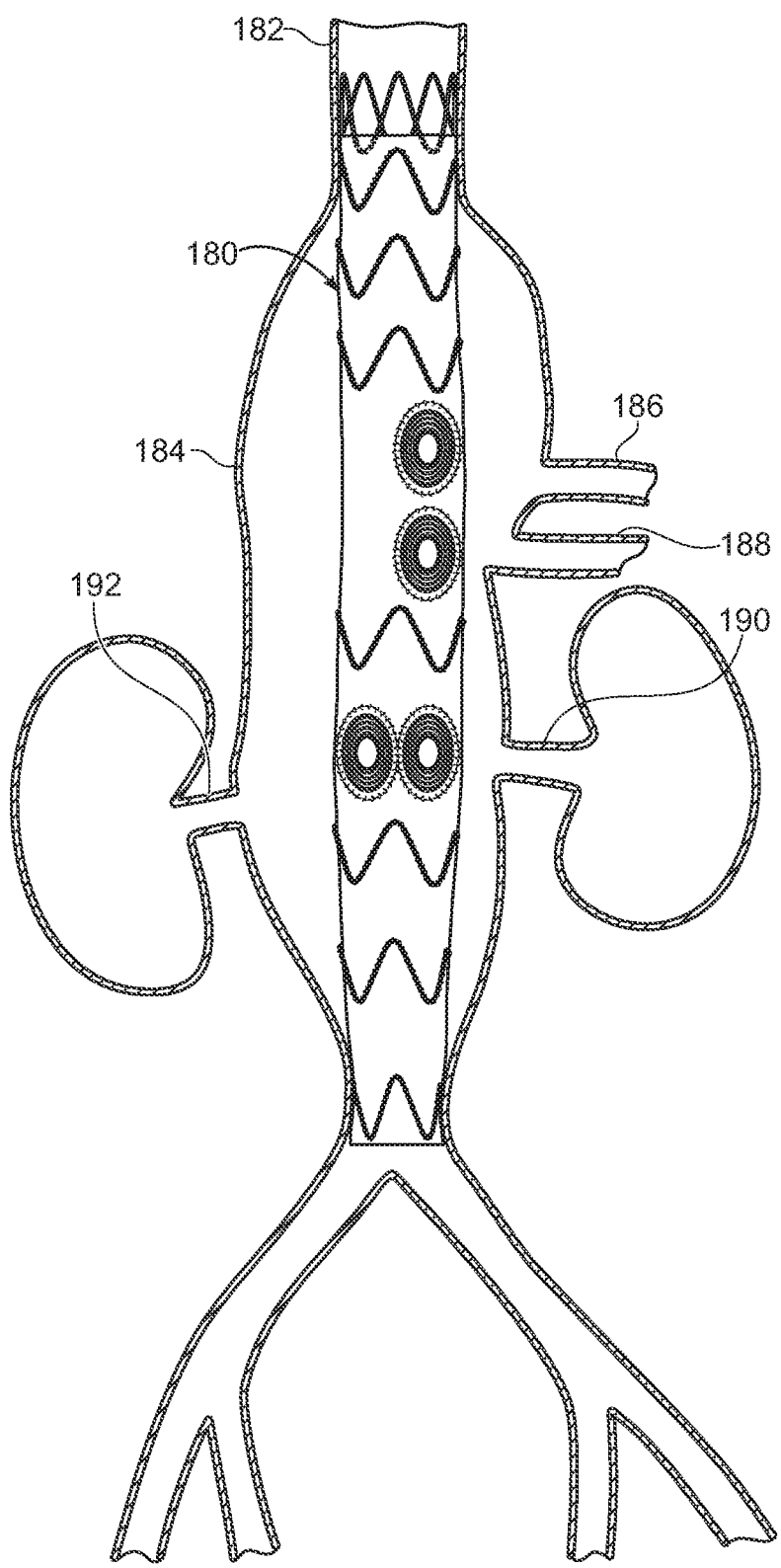
FIG. 12 is a side view of an embodiment of a vascular prosthesis of the invention implanted at an aortic aneurysm of a subject.
Figure 13:
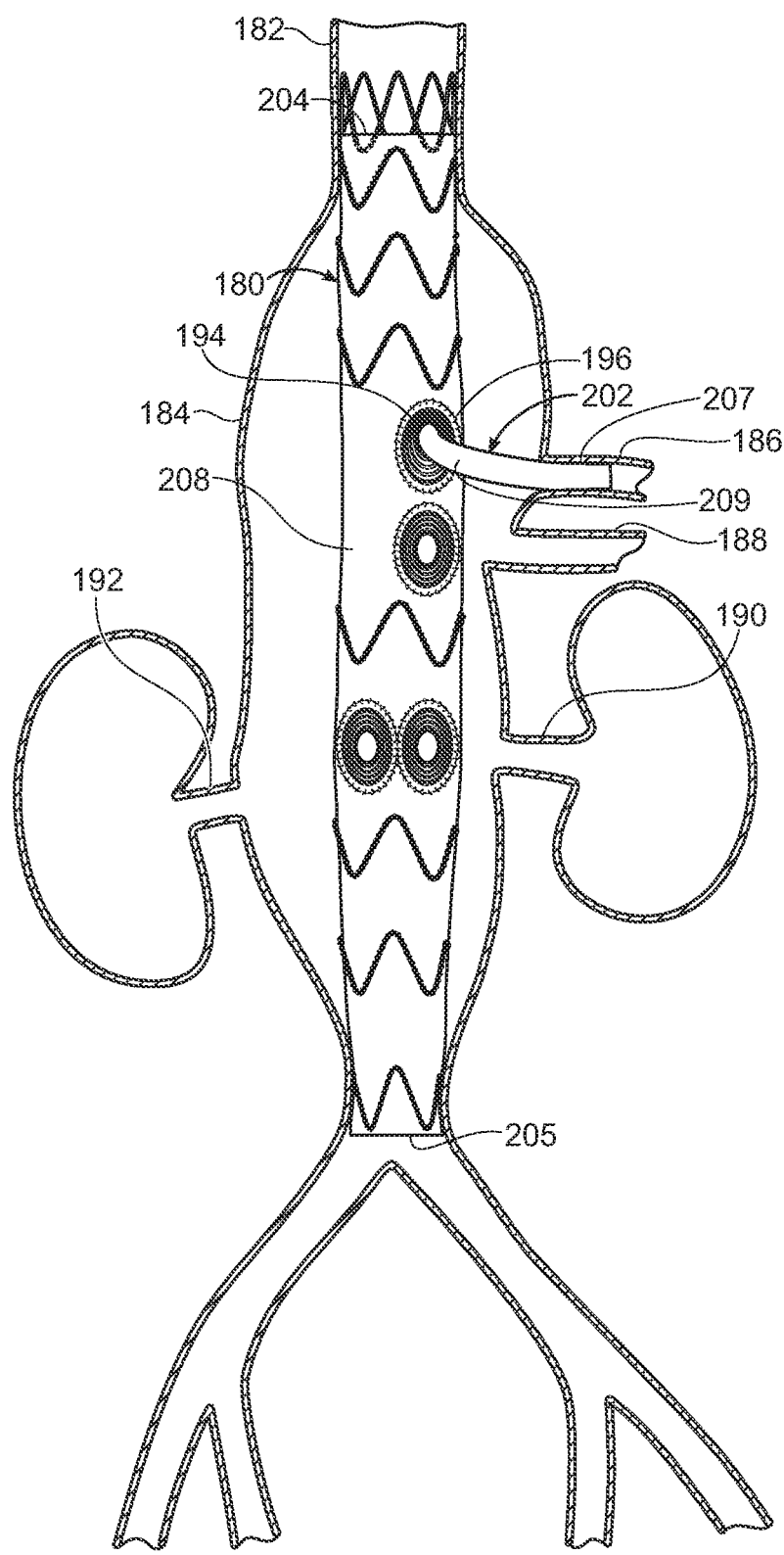
FIG. 13 is a side view of the vascular prosthesis shown in FIG. 12, with one branch prosthesis having been implanted through a fenestration and through an opening defined by the associated crimped adapter of the vascular prosthesis shown in FIG. 12.

In another embodiment, the invention is a method for treating an aortic aneurysm. For example, with reference to FIG. 12, vascular prosthesis 180 is delivered through aorta 182 to aortic aneurysm 184 of a patient, such as by radially and releasably constraining vascular prosthesis 180 by a vascular prosthesis delivery device, not shown. In this embodiment shown in FIG. 12, aneurysm site 184 spans a region of the aorta that includes the celiac artery 186, the superior mesenteric artery 188, and left and right renal arteries 190, 192, respectively. Vascular prosthesis includes four fenestrations, each of which includes an associated crimped adapter which is substantially aligned with a corresponding arterial branch of the aorta at the aneurysm site of the patient. Vascular prosthesis 180 is then released from the vascular delivery device and the delivery device is removed from the patient. As shown in FIG. 13, branch prosthesis 202 is delivered by the branch prosthesis delivery device (not shown) through proximal open end 204 or distal open end 205 of luminal graft component 208 of the vascular prosthesis 180. Branch prosthesis 202 is then directed through fenestration 194 and the associated crimped adapter 196, and distal end 207 of branch prosthesis 202 is implanted in celiac artery 186. Proximal end 209 of branch prosthesis 202 is fixed at opening of crimped adapter 196.

The vascular prosthesis of the invention, and the branch prosthesis included in vascular prosthesis assemblies of the invention can be implanted by, for example, a delivery device, such as is known in the art.

FIG. 14 is an exploded side view of a prior art delivery device suitable for delivering a vascular prosthesis of the invention or a branch prosthesis. As can be seen in FIG. 14, delivery device 230 includes guidewire catheter 232 having proximal end 234 and distal end 236. Proximal handle 238 is fixed to proximal end 234 and nose cone 240 is fixed to distal end 236. Introducer sheath 242 has proximal end 244 and distal end 246. Distal handle 248 is fixed to proximal end 244. Introducer sheath 242 can be rigid or flexible.

FIG. 15A is a side view of delivery device 230 when assembled containing vascular prosthesis of the invention (not shown) within introducer sheath 242 of delivery system 230. As can be seen therein, introducer sheath 242 and distal handle 248 extend around guidewire catheter 232. Although not shown, a vascular prosthesis of the invention is held in a radially constrained position around guidewire catheter 232 and within introducer sheath 242. The vascular prosthesis is implanted at an arterial aneurysm by advancing delivery device 230 within an artery of a patient until the vascular prosthesis is at the arterial aneurysm 231 spanning arterial branch 233. Distal handle 248 is then retracted along guidewire catheter 232 and toward proximal handle 238 in the direction of arrow 235, as shown in FIG. 15B, thereby retracting introducer sheath 242 from around vascular prosthesis 250. In another embodiment, delivery device 230 is advanced in an artery to position distal to arterial aneurysm 231, and proximal handle 230 is advanced in a distal direction indicated by arrow 237 to thereby direct guidewire 232 and vascular prosthesis 250 to a position spanning arterial aneurysm 231, as shown in FIG. 15B. Vascular prosthesis 250 with at least one crimped adapter and opening 251 is released from its radially constrained position and radially expands to a released position, such as by use of a balloon catheter, or by use self-expanding radial stents, as is known in the art, and is thereby deployed at the arterial aneurysm 231. Delivery device 230 thereafter is removed from the patient, as shown in FIG. 15C, thereby completing implantation of vascular prosthesis 250 and treatment of the aortic aneurysm. The same or a similar delivery device can be employed to deliver or implant branch prosthesis 253 through 251 of a vascular prosthesis 250 of the invention. It is to be understood that, alternatively, other suitable types of aortic prosthesis delivery devices, such as are known in the art, can be employed.

Figure 16:
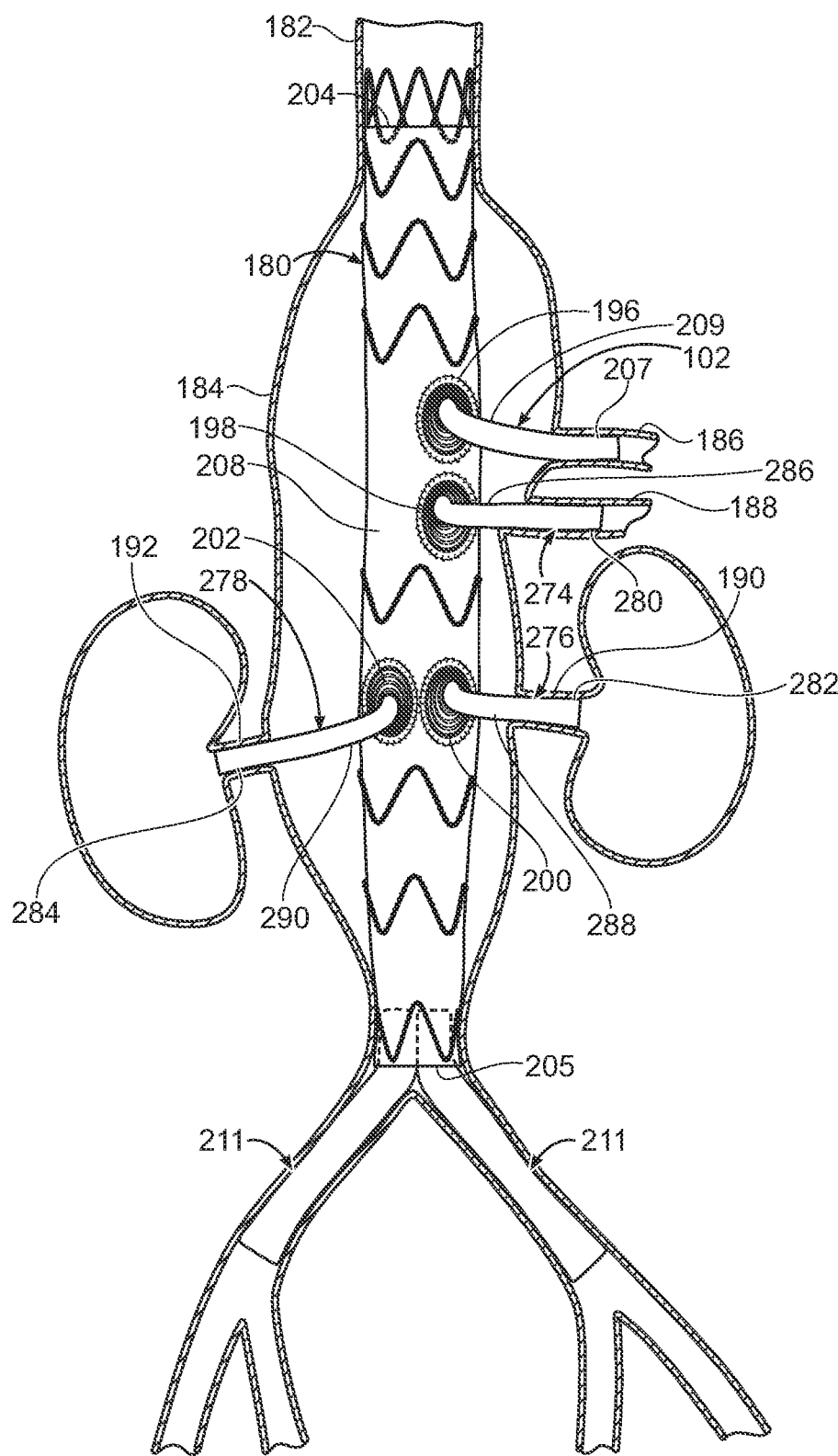
FIG. 16 is a side view of the vascular prosthesis of FIGS. 12 and 13, wherein branch prostheses have been implanted through respective fenestrations and openings defined by associated crimped adapters of the vascular prosthesis of the invention.

As can be seen in FIG. 16, in addition to implantation of branch prosthesis 102, as shown in FIG. 13, branch prostheses 274, 276, 278 are delivered through each corresponding fenestration and extend from each corresponding fenestration. Distal ends 280, 282, 284 are each directed by a respective branch prosthesis delivery device (not shown) into a respective branches 188, 190, 192 of aorta 182 at aortic aneurysm 184, and secured in respective fenestrations by a crimped adapters 198, 200, 202 at proximal ends 286, 288, 290 within branch artery 188, 190, 192, at the distal ends 280, 282, 284. Proximal ends 286, 288, 290, of respective branch prosthesis 274, 276, 278, are fixed at respective fenestrations. Each branch prosthesis 274, 276, 278, is then released from the respective branch prostheses delivery device. The vascular prosthesis delivery device and the branch prosthesis delivery device are then removed either simultaneously or, in sequence, thereby completing implantation and treatment of the aortic aneurysm. In an embodiment, additional branch prostheses 211 can be implanted at distal end 205 of vascular prosthesis 180, as is also shown in FIG. 16.

Although not shown, the distal end of vascular prostheses of the invention can be bifurcated and additional prostheses can be implanted into the distal end of the bifurcated vascular prosthesis.

Vascular prostheses of the invention can be implanted, for example, by transfemoral access. Additional branch prostheses that are directed into the vascular prostheses of the invention can be implanted, for example, by supraaortic vessel access (e.g., through the brachial artery), or by transfemoral access, or access from some other branch or branch of major blood vessels, including peripheral blood vessels.

The teachings of all patents, published applications and references cited herein are incorporated by reference in their entirety. The relevant teachings of U.S. Pat. Nos. 8,292,943; 7,763,063; 8,308,790; 8,070,790; 8,740,963; 8,007,605; 9,320,631; 8,062,349; 9,198,786; 8,062,345; 9,561,124; 9,173,755; 8,449,595; 8,636,788; 9,333,104; 9,408,734; 9,408,735; 8,500,792; 9,220,617; 9,364,314; 9,101,506; 8,998,970; 9,554,929; 9,439,751; 9,592,112; 9,655,712; 9,827,123, 9,877,857, 9,907,686; U.S. patent application Ser. Nos. 14/575,673; 15/166,818; 15/167,055; 14/272,818; 14/861,479; 15/478,424; 15/478,737; 15/587,664; 15/604,032; 15/672,404; 15/816,772; 15/839,272; 15/417,467; PCT/US2017/025844; PCT/US2017/025849; PCT/US2017/025912; PCT/US2017/034223 and PCT/US2017/046062, are also incorporated by reference in their entirety.

The relevant teachings of International Application Numbers PCT/US2018/019355; PCT/US2018/019344; PCT/US2018/019349; PCT/US2018/019353; PCT/US2018/019354; PCT/US2018/019352; PCT/US2018/019342; PCT/US2018/019350; PCT/US2018/019351; and PCT/US2018/019510 are also incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A vascular prosthesis, comprising:
a) a luminal graft component having a proximal open end, a distal open end, and defining a main lumen extending from the proximal open end to the distal open end, the luminal graft component defining at least one fenestration; and
b) a crimped adapter at the at least one fenestration, the crimped adapter including a perimeter section that is fixed to the luminal graft component and seals the fenestration, the crimped adapter also defining an opening with a diameter smaller than the fenestration and including a crimped portion of generally concentric folds arranged concentrically within the perimeter section and about the opening,
wherein the concentric folds are coplanar, and
whereby the crimped adapter can adapt to positioning of a branch prosthesis extending through the opening by flexation of the folds to thereby move the opening relative to the perimeter section, and
wherein the concentric folds of the crimped adapter have a periodicity of about 1 mm to about 5 mm.

2. The vascular prosthesis of claim 1, wherein the concentric folds of the crimped adapter have an amplitude in a range of between about 1 mm and about 10 mm.

3. The vascular prosthesis of claim 1, wherein the perimeter section of the crimped adapter includes first surface, with a crimped portion raised from the first surface.

4. The vascular prosthesis of claim 3, wherein the first surface faces an outside surface of the luminal graft component.

5. The vascular prosthesis of claim 3, wherein the folds of the crimped adapter have a period in a range of between about 2 mm to about 4 mm.

6. The vascular prosthesis of claim 1, wherein the crimped adapter includes between about 3 folds to about 10 folds.

7. The vascular prosthesis of claim 1, wherein the crimped portion is circular.

8. The vascular prosthesis of claim 1, wherein the crimped portion is round.

9. The vascular prosthesis of claim 1, wherein the crimped portion is oval.

10. The vascular prosthesis of claim 1, wherein the crimped portion is elliptical.

11. The vascular prosthesis of claim 1, wherein the crimped portion is rectangular.

12. The vascular prosthesis of claim 1, wherein the crimped portion is rectilinear.

13. The vascular prosthesis of claim 1, wherein the crimped adapter includes a ring affixed to a circumference thereof.

14. The vascular prosthesis of claim 1, further including a plurality of radial stents distributed longitudinally along the luminal graft component, the radial stents including struts that define proximal apices and distal apices.

15. The vascular prosthesis of claim 1, wherein the crimped adapter includes at least one member selected from the group consisting of polytetrafluoroethylene, polyethylene terephthalate, polymer and silicon.

16. The vascular prosthesis of claim 1, wherein the vascular prosthesis includes one fenestration and one crimped adapter.

17. The vascular prosthesis of claim 1, wherein the vascular prosthesis includes two fenestrations and two or more crimped adapters.

18. The vascular prosthesis of claim 1, further including at least one branch prosthesis, each branch prosthesis having a proximal end and a distal end, and extendable through the opening of the crimped adapter and the fenestration of the luminal graft component.

* * * * *